United States Patent [19]

Mendenhall et al.

[11] Patent Number: 4,595,784

[45] Date of Patent: Jun. 17, 1986

[54] HYDROCARBON FUEL ADDITIVES AND METHOD FOR PREPARING SAME

[75] Inventors: G. David Mendenhall, Hancock; Hsiang T. Chen, Houghton, both of Mich.

[73] Assignee: Board of Control of Michigan Technological University, Houghton, Mich.

[21] Appl. No.: 669,096

[22] Filed: Nov. 7, 1984

[51] Int. Cl.$^4$ .............................................. C07C 45/00
[52] U.S. Cl. ........................................ 568/387; 44/56; 44/57; 44/77; 568/840; 568/902
[58] Field of Search .................... 568/387, 840, 902; 44/57, 77, 56

[56] References Cited

U.S. PATENT DOCUMENTS

| | | | |
|---|---|---|---|
| 1,907,309 | 5/1933 | Van Schaack, Jr. | 44/56 |
| 2,078,736 | 4/1937 | Schurink | 44/56 |
| 2,087,582 | 7/1937 | Schneider | 44/56 |
| 2,262,817 | 11/1941 | Peck | 568/387 |
| 3,356,720 | 12/1967 | Mirviss et al. | 568/387 |
| 3,822,119 | 7/1974 | Frech et al. | 44/56 |
| 4,083,880 | 4/1978 | Kagan et al. | 568/840 |

*Primary Examiner*—Mrs. Y. Harris-Smith

[57] ABSTRACT

A compound having the general formula $R_xCOH[COR]_y$, wherein R is a lower alkyl hydrocarbon radical, y is 0 or 1, and x is 2 when y is 1 and 3 when y is 0, is prepared by admixing carbon monoxide, a transition metal halide, and an organomonolithium compound or an anionic equivalent thereof.

9 Claims, No Drawings

HYDROCARBON FUEL ADDITIVES AND METHOD FOR PREPARING SAME

BACKGROUND OF THE INVENTION

This invention relates to cetane-enhancing additives for hydrocarbon fuels used in internal combustion engines and methods for preparing same.

Various cetane-enhancing compounds have been used as additives for improving the combustion efficiency of hydrocarbon fuels, such as diesel fuel, used in internal combustion engines. Three-tert-butyl-3-hydroxy-2,2,5,5-tetramethyl-4-hexano ne is a known compound. However, to the best of applicant's knowledge, neither it nor analogs thereof have been used as cetane-enhancing additive for improving the combustion efficiency of hydrocarbon fuels used in internal combustion engines. Methods for preparing the above compound are disclosed by F. J. Abruscato and T. T. Tidwell, *J. Org Chem,* 37, 4151–4156 (1972). These methods involve the addition of tert-butyllithium to pivalil or to di-tert-butylacetyl chloride. Both of the latter compounds are difficult to prepare. Consequently, these methods make the resulting product too costly for wide use as a cetane-enhancing additive for diesel fuels and the like.

SUMMARY OF THE INVENTION

One of the objects of the invention is to improve the combustion efficiency of hydrocarbon fuels used in internal combustion engines by adding thereto an effective amount of a cetane-enhancing compound.

Another object of the invention is to provide a simple, inexpensive method for preparing such compounds.

Another object of the invention is to provide a one-step, catalyzed method for alkylating carbon monoxide.

Other objects, aspects and advantages of the invention will become apparent to those skilled in the art upon reviewing the following detailed description and the appended claims.

Compounds having the general formula $R_xCOH[COR]_y$, wherein R is a lower alkyl hydrocarbon radical, y is 1 or 0, and x is 2 when y is 1 and 3 when y is 0, are prepared by admixing carbon monoxide with a transition metal halide and an organomonolithium compound having the general formula RLi or an anionic equivalent thereof.

Carbon monoxide can be alkylated in one step by contacting it with a mixture of tert-butyllithium and titanium tetrachloride.

DESCRIPTION OF THE PREFERRED EMBODIMENTS

Compounds having the above general formula contain one OH group and only primary hydrogens which render them less susceptible to oxidative attack during storage then hydrocarbon fuels. They are highly soluble in hydrocarbon fuels, such as diesel fuel, and are insoluble in and inert to water. While their behavior as a hydrocarbon fuel additive is not completely understood at this time, it is believed that, upon being heated, such compounds undergo a facile fragmentation into radicals which can initiate chain reactions during the compression strokes of an internal combustion engine, resulting in the ignition of the fuel.

While various transition metal halides can be used, the halides of the transition metals in Group IV to VIII of the periodic table are preferred. Representative preferred transition metals include titanium tetrachloride, titanium trichloride, zirconium tetrachloride, gallium bromide, and samarium chloride, lanthanum trichloride, indium trichloride and vanadium tetrachloride, with titanium tetrachloride and titanium trichloride being the most preferred at this time.

The organomonolithium compounds used have the general formula RLi with R being a lower alkyl hydrocarbon radical, preferably a saturated alkyl containing from 1 to 20 carbon atoms. Suitable organomonolithium compounds include methyllithium, n-butyllithium, and tert-butyllithium, n-octolithium, benzllithium, and phenyethyllithium, with tert-butyllithium being preferred.

Suitable anionic equivalents of the organomonolithium compounds include those having the general formula RNa, $R_2Zn$, and $RM_gX$ wherein X is a halogen, such as benzl sodium, n-butyl magnesium chloride, and dimethyl zinc.

While various suitable reaction schemes can be followed, the organomonolithium compound and the transition metal halide preferably are first dissolved in a suitable solvent and appropriate amounts of these solvents are used to provide the desired mole ratio of organomonolithium to transition metal halide, which is preferably at least 8:1. Suitable solvents for the organomonolithium compounds include inert hydrocarbons, such as pentane, hexane, heptane, and ether. Suitable solvents for the transition metal halides and the anionic equivalents thereof include the same inert hydrocarbons and chlorinated solvents, such as methylene chloride, when used at lower temperatures of about $-30°$ C. or less.

These solutions preferably are mixed in the presence of a suitable inert hydrocarbon diluent, such as pentane, hexane, and heptane. This mixing step is usually carried out at a reduced temperature of at least about $-30°$ C. or lower and under an atmosphere of an inert gas such as argon. The resulting mixture is contacted with carbon monoxide while the mixture is maintained at a reduced temperature of at $-50°$ C., such as by flushing the reaction vessel with carbon monoxide or by incrementally injecting carbon monoxide into the mixture. The amount of carbon monoxide used preferably is at least stoichiometric. An excess is usually used when carbon monoxide is added by flushing.

By varying the reaction conditions, the reaction product can contain a mixture of two different compounds falling within the above general formula, one wherein x is 2 and y is 1, such as 3-tert-butyl-3-hydroxy-2,2,5,5- tetramethyl-4-hexanone; and another where x is 3 and y is 0, such as tri-tert-butyl carbinol. Higher yields of the latter type compound is usually obtained when a stoichiometric amount of carbon monoxide is slowly injected into the mixture. These two compounds can be recovered from the reaction medium in any suitable manner.

Without further elaboration, it is believed that one skilled in the art, using the foregoing description, can utilize the present invention to its fullest extent. The following example is presented to exemplify a preferred embodiment of the invention and should not be construed as a limitation thereof.

EXAMPLE 0.8 ml of a methylene chloride solution containing titanium tetrachloride (0.008 mole $TiCl_4$), 32 ml of a pentane solution containing tert-butyllithium (0.064 mole t-C$_4$H$_9$Li) and 20 ml of pentane were added to a reaction vessel and mixed under an atmosphere of argon at a temperature of about −30° to about −50° C. for one hour. The reaction vessel was flushed with a stoichiometric excess of carbon monoxide for 30 minutes while the reaction vessel was maintained at a temperature of −70° to −90° C. and then allowed to return to room temperature.

The reaction product was hydrolyzed and acidified with 20% sulfuric acid to produce an organic layer which was separated from the remaining solution. This organic layer was introduced into silica column and resolved into two fractions.

One fraction containing higher molecular weight components was passed through an alumina column and resolved into two components. One component was in the form of needle crystals found to have a melting point of approximately 113°–115.50° C. and IR and NMR analyses indicated that it had the following formula: (t-C$_4$H$_9$)$_2$C(OH)COC$_4$H$_9$-t.

IR and NMR analyses of the other component indicated that it had the following formula: [(CH$_3$)$_3$]$_3$COH.

Similar tests have been made with a stoichiometric amount of carbon monoxide being slowly injected into the starting mixture with a syringe, while the mixture is being stirred, instead of flushing the reaction vessel with an excess of carbon monoxide as described above. Otherwise, the same reaction conditions and separation schemes were followed. It has been found that incremental injection of carbon monoxide in this manner generally produces higher yields of tri-tert-butyl carbinol.

From the foregoing description and example, it can be seen that the invention provides a simple, inexpensive method for preparing compounds which can be used as a cetane-enhancing additive for hydrocarbon fuels. It can also be seen that the invention provides a simple one-step, catalyzed method for alkylating carbon monoxide.

One skilled in the art can easily ascertain the characteristics of the method and, without departing from the spirit and scope of the invention, make various changes and modifications to adapt it to various usages.

We claim:

1. A method for preparing a compound having the general formula:

wherein
R is a lower alkyl hydrocarbon radical,
y is 0 or 1, and
x is 2 when y is 1 and 3 when y is 0.
said method comprising admixing carbon monoxide, a transition metal halide, and an organomonolithium compound having the general formula RLi or an anionic equivalent thereof, wherein R is the same as above, and recovering said compound from the resulting reaction product.

2. The method according to claim 1 wherein said transition metal is in Group IV to VIII of the periodic table.

3. The method according to claim 2 wherein R is a saturated alkyl containing from 1 to 20 carbon atoms.

4. The method according to claim 3 wherein said anionic equivalent is RNa, RMgX wherein X is a halogen, or R$_2$Zn.

5. The method according to claim 3 wherein said transition metal halide is titanium tetrachloride or titanium trichloride.

6. The method according to claim 5 wherein said organomonolithium compound is tert-butyllithium.

7. The method according to claim 6 wherein said compound is 3-tert-butyl-3-hydroxy-2,2,5,5-tetramethyl-4-hexanone.

8. The method according to claim 6 wherein said compound is tri-tert-butyl carbinol.

9. A method for alkylating carbon monoxide comprising the step of contacting carbon with a mixture of tert-butyllithium and titanium tetrachloride.

* * * * *